United States Patent
Basso et al.

(10) Patent No.: US 9,700,547 B2
(45) Date of Patent: Jul. 11, 2017

(54) USE OF 6-HYDROXY-2-PYRIDONES AND DERIVATIVES THEREOF FOR PREPARING A PHARMACEUTICAL COMPOSITION THAT ACTS BY INHIBITING THE HUMAN URIDINE PHOSPHORYLASE ENZYME

(71) Applicant: UNIÃO BRASILEIRA DE EDUCAÇÃO E ASSISTÊNCIA, MANTENEDORA DA PUCRS, Porto Alegre (BR)

(72) Inventors: Luiz Augusto Basso, Porto Alegre (BR); Pablo Machado, Porto Alegre (BR); Daiana Renck, Porto Alegre (BR); Diógenes Santiago Santos, Porto Alegre (BR)

(73) Assignee: União Brasileira de Educação e Assistência, Mantenedora da Pucrs, Porto Alegre (BR)

( * ) Notice: Subject to any disclaimer, the term of this patent is extended or adjusted under 35 U.S.C. 154(b) by 0 days.

(21) Appl. No.: 14/916,152

(22) PCT Filed: Sep. 2, 2014

(86) PCT No.: PCT/BR2014/000307
§ 371 (c)(1),
(2) Date: Mar. 2, 2016

(87) PCT Pub. No.: WO2015/031968
PCT Pub. Date: Mar. 12, 2015

(65) Prior Publication Data
US 2016/0193197 A1    Jul. 7, 2016

(30) Foreign Application Priority Data
Sep. 3, 2013 (BR) .......................... 102013022567

(51) Int. Cl.
*A61K 31/4412* (2006.01)
*A61K 31/513* (2006.01)
*A61K 31/4545* (2006.01)

(52) U.S. Cl.
CPC ...... *A61K 31/4412* (2013.01); *A61K 31/4545* (2013.01); *A61K 31/513* (2013.01)

(58) Field of Classification Search
CPC .............. A61K 31/4412; A61K 31/513; A61K 31/4545
See application file for complete search history.

(56) References Cited

U.S. PATENT DOCUMENTS

| 4,613,604 A | 9/1986 | Chu |
| 5,155,113 A | 10/1992 | Fujii |
| 5,567,689 A | 10/1996 | Sommadossi |
| 5,968,914 A * | 10/1999 | von Borstel ......... A61K 31/513 |
| | | 514/269 |

OTHER PUBLICATIONS

Iltzsch et al. Biochemical Pharmacology (1993), 46(10), p. 1849-58.*
Stopper et al., Combination of the chemotherapeutic agent 5-fluorouracil with an inhibitor of its catabolism results in increased micronucleus induction, Biochem. Biophys. Res. Commun., Sep. 15, 1994, 203(2):1124-30.

* cited by examiner

*Primary Examiner* — Yong Chu
(74) *Attorney, Agent, or Firm* — Laurence P. Colton; Smith Tempel Blaha LLC

(57) ABSTRACT

The use of at least one compound of formula I or II or pharmaceutically acceptable salts thereof, for preparing a pharmaceutical composition that acts by inhibiting the phosphorylase uridine enzyme, and the use of the compounds for preparing a pharmaceutical composition that acts by inhibiting the human phosphorylase uridine enzyme, which can be optionally used in combination with at least one antineoplastic, wherein the inhibition increases the effectiveness of antineoplastic and decreases the side effects caused by the administration of antineoplastics.

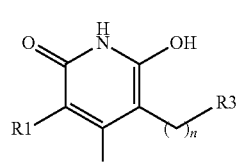

Formula I

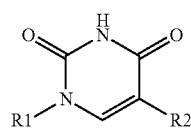

Formula II

11 Claims, 5 Drawing Sheets

USE OF 6-HYDROXY-2-PYRIDONES AND DERIVATIVES THEREOF FOR PREPARING A PHARMACEUTICAL COMPOSITION THAT ACTS BY INHIBITING THE HUMAN URIDINE PHOSPHORYLASE ENZYME

BACKGROUND OF THE INVENTION

Field of the Invention

The present invention describes the use of chemical compounds in the preparation of a pharmaceutical composition that acts by inhibiting the phosphorylase uridine enzyme. Particularly, the present invention comprises the use of the compounds of formula I or II, alone or in combination with at least one antineoplastic for the preparation of a pharmaceutical composition that acts by inhibiting the phosphorylase uridine enzyme, wherein the inhibition acts, for example, in the antineoplastic effectivity increase and in the side effects reduction caused by the antineoplastic administration. The present invention is found in the fields of chemistry, pharmacy and medicine.

Prior Art

The human phosphorylase uridine enzyme (EC 2.4.2.3) is one of the promising targets for the study and development of new chemical compounds with capacity of increasing uridine (Urd) endogenous levels by inhibiting the catalyzed chemical reaction by the protein. A class of inhibitor compounds of this enzyme is the one of the derivatives of 6-hydroxy-2-pyridones, which have been tested regarding the several pathologies, including neurodegenerative, heart and neoplasia diseases. However, the technical challenges remaining for achieving the structures of this compounds class, in special compounds that present an increased specific enzymatic inhibition and, at the same time, act in a combined manner with other drugs, in special the drugs for treating cancer, which are known by their several undesirable side effects, as the weight loss and inflammatory toxic reactions, as the mucositis.

Among the compounds known for oncological treatment, it is included the 5-fluorouracil, which main side effects caused are: alopecia, weight loss, diarrhea and mucositis, this latter either intestinal as oral. Due to these side effects, the patients stop their treatments because the severe pains and because the feeding impossibility due to oral ulcers. It is in this context that the search for new combined chemotherapies regimens become important.

The document of Stopper et al ("Combination of the chemotherapeutic agent 5-fluorouracil with an inhibitor of its catabolism results in increased micronucleus induction", *Biochem Biophys Res Commun.* 1994 Sep. 15; 203(2):1124-30) discloses that the necessary concentration of 5-fluorouracil may be reduced on half for achieving the genotoxic effect in the presence of the chemotherapeutic 2,6-dihydroxypiridine. It is also disclosed that the combined application of 5-fluorouracil and one inhibitor, 2,6-dihydropyridine, for example, it reduces the side effects of the antineoplastic by reducing the chemotherapeutic effective dose.

The present invention differs from this document by the fact that it discloses the use of compounds originated from 6-hydroxy-2-pyridones different from that disclosed in Stopper et al. and which action mechanism is also different, by having as target the human phosphorylase uridine enzyme (hUP, EC 2.4.2.3). The present invention also differs from this document by enabling the amount reduction of 5-fluorouracil that is converted to 5-fluorouridine and 5-fluorouridine monophosphate.

The search in the patent literature indicated some relevant documents that will be described below.

The document U.S. Pat. No. 5,155,113 discloses that the combined therapy of 5-fluorouracil (or some compound able to produce in vivo 5-fluorouracil) with one derived from pyridine, as defined in U.S. Pat. No. 5,155,113, would be able of potentiate the anticancer activity of the 5-fluorouracil.

The present invention differs from this document by the fact of proposing the use of different compounds from class 6-hydroxy-2-pyridones and that are used in a combined therapy with anti-tumor drugs, as the 5-fluorouracil. In addition, the action mechanism of the compounds used in the present invention (inhibiting the phosphorylase uridine) is different from those disclosed in U.S. Pat. No. 5,155,113.

The document U.S. Pat. No. 4,613,604 discloses a pharmaceutical composition having phosphorylase uridine enzyme inhibitors, wherein they increase the anti-tumor effectivity of pyrimidine nucleotides, as the 5-fluorouracil and that do not interfere with the normal cells growth of the patient.

The present invention differs from this document by the fact of presenting inhibitor compounds of the human phosphorylase uridine with structure different from those described in the document U.S. Pat. No. 4,613,604. While the document U.S. Pat. No. 4,613,604 discloses compounds originated from pyrimidines, the present invention discloses derivatives from pyridines. In addition, the document U.S. Pat. No. 4,613,604 does not disclose neither suggests a solution for the side effects caused by antineoplastic.

The document U.S. Pat. No. 5,567,689 discloses methods and pharmaceutical compositions for increasing uridine levels in the plasma and intracellular, with compounds dilazep, hexobendine, L-uridine; L-2'-3'-dideoxiuridine, and D-2',3'-dideoxiuridine.

The present invention differs from this document by the fact of presenting the use of distinct compounds and the document U.S. Pat. No. 5,567,689 does not disclose or suggest the combination of these compounds with antineoplastic.

In this way, there is the need of searching for compounds having increased capacity of inhibiting the phosphorylase uridine enzyme, inhibiting this may prevent or reduce the amount of side effects caused by antineoplastic, or, further, be used in the therapeutic of several diseases in which the uridine endogenous increase by being a therapeutic alternative for current treatments.

According to searched literature, documents anticipating or suggesting the present invention teachings were not found, in a way that the solution here proposed has novelty and inventive activity against the state of the art.

BRIEF SUMMARY OF THE INVENTION

In one aspect, the present invention provides the use of a compound of formula I or II,

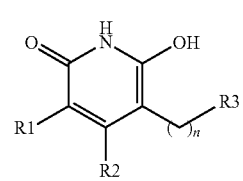

Formula I

-continued

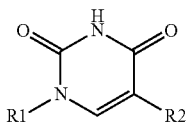

Formula II or its pharmaceutically acceptable salts
wherein, for the formula I, R1, R2, and R3 are independently chosen among:
R1=H, $NO_2$, CN, $CO_2H$, $NH_2$, halogens, alkyl, aryl, or heteroaryl;
R2=H, $NO_2$, CN, $CO_2H$, $NH_2$, halogens, alkyl, aryl, heteroaryl, alcohols, or esters;
R3=H, $NO_2$, CN, $CO_2H$, $NH_2$, halogens, alkyl, aryl, heteroaryl, amino alcohols, amino alkyls, alcohols, or esters;
and, wherein for the formula II:
R1=H and R2=—$CH_2NHCH_2CH_2OH$
when preparing a pharmaceutical composition that acts by inhibiting the human phosphorylase uridine enzyme.

In a preferred embodiment of the use of the present invention, the pharmaceutical composition comprises the compound of formula I or II individually or combined with at least one antineoplastic.

In a preferred embodiment of the use of the present invention, in the formula I compounds, R1, R2, and R3 are independently chosen among:
a) when R1=CN, R2=$CH_3$ and n=1, R3=—$N(CH_3)_2$, —$NHCH_2CH_2OH$, H, (1,2-dihydroxypropan-3-yl) amino, piperidin-1-yl, (1,3-dihydroxypropan-2-yl) amino, —$N(CH_2CH_3)_2$, —$N(CH_2CH_2CH_3)_2$, or phenyl;
b) R1=CN, R2=phenyl, R3=H, and n=0;
c) R1=CN, R2=$CH_2CH_3$, R3=H, and n=0;
d) R1=CN, R2=H, R3=H, and n=0;
e) R1=CN, R2=$CH_3$, n=0, and the counter-ion of the formula I is $K^+$.

In a preferred embodiment of the use of the present invention, the compound has the formula X, Y, or Z:

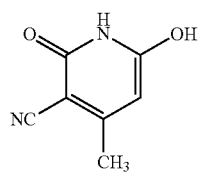

Formula X

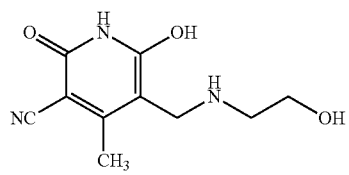

Formula Y

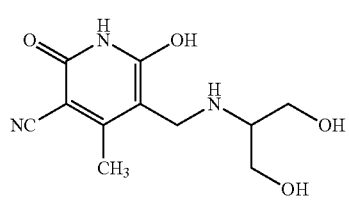

Formula Z

In a preferred embodiment of the use of the present invention, the compound of formula X is in a concentration range from 300 nM to 600 nM, the compound of formula Y is in a concentration range from 58 nM to 78 nM, and the compound of formula Z is in a concentration range from 83 nM to 105 nM regarding the inhibition of the human phosphorylase uridine enzyme catalytic activity.

In another preferred embodiment of the use of the present invention, the present invention refers to the use of formulas I or II compounds when preparing a pharmaceutical composition that acts by inhibiting the human phosphorylase uridine enzyme, wherein the inhibition acts in the antineoplastic effectivity increase.

In another preferred embodiment of the use of the present invention, the present invention refers to the use of formulas I or II compounds when preparing a pharmaceutical composition that acts by inhibiting the phosphorylase uridine enzyme, wherein inhibition acts in the side effects reduction caused by the antineoplastic administration.

In a preferred embodiment of the use of the present invention, the side effect is the mucositis.

In a preferred embodiment of the use of the present invention, the antineoplastic is a pyrimidine analogue.

In a preferred embodiment of the use of the present invention, the antineoplastic is a fluoropyrimidine.

In a preferred embodiment of the use of the present invention, the antineoplastic is the 5-fluorouracil or the 5-fluoro-2'-deoxyuridine.

In a preferred embodiment of the use of the present invention, the 5-fluorouracil is in a concentration ranging from 100 $mg/m^2$ of body surface to 600 $mg/m^2$ of body surface.

In a preferred embodiment of the use of the present invention, the inhibition of the phosphorylase uridine enzyme acts in the treatment of physiological disorders group consisting of: epilepsy, convulsions, Parkinson disease, Alzheimer disease, anxiety, sleeping disorders, infertility, ischemia, hypoxia, respiratory dysfunction, cardiovascular diseases, and hand-foot syndrome (palmar-plantar erythrodysesthesia) induced by chemotherapy.

Those and other objects of the invention are immediately appreciated by those people skilled in the art and by the companies interested in the segment and are described in enough details in the following description.

DETAILED DESCRIPTION OF PREFERRED EMBODIMENTS

Figure 1:
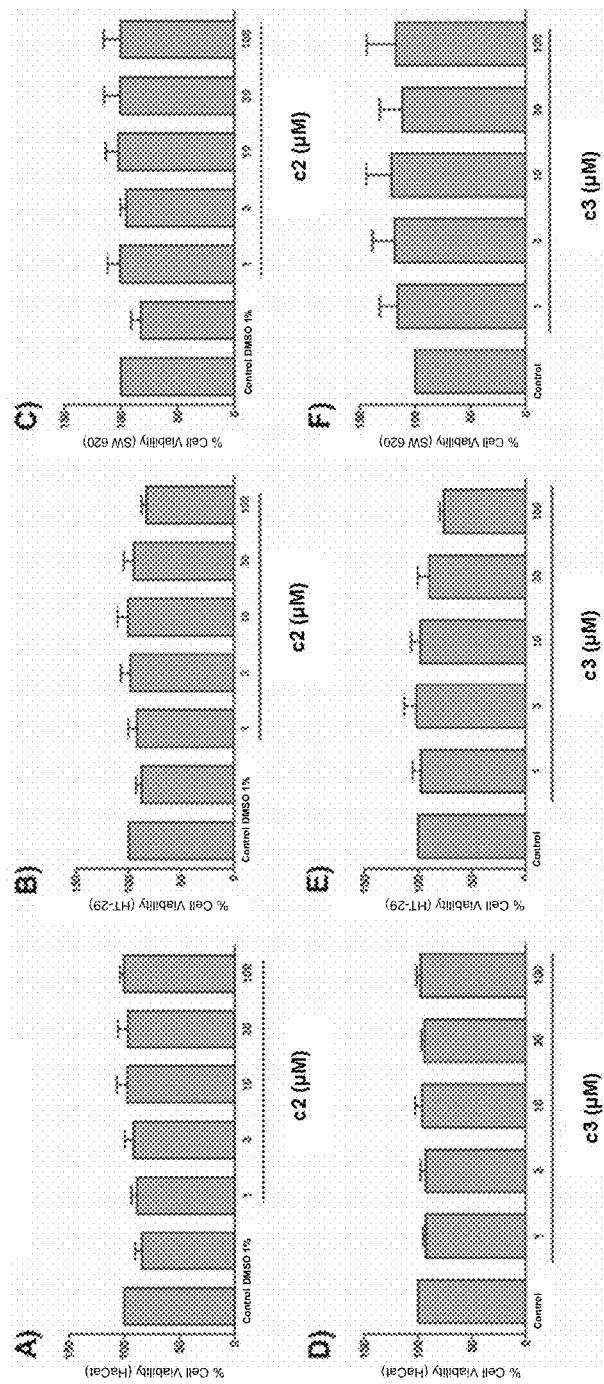
FIG. 1 shows the cytotoxicity evaluation of the compounds c2 and c3 in cell culture.

In the context of the present invention, the term "antineoplastic" must be understood as any isolated drug or combined with other compounds acting direct or indirectly in the cancer cells death.

Use of the formulas I or II compounds as phosphorylase uridine enzyme inhibitors.

Formula I or II compounds:

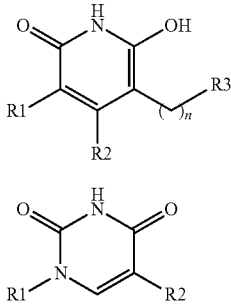

Formula I

Formula II or its pharmaceutically acceptable salts
wherein, for the formula I, R1, R2, and R3 are independently chosen among:
- R1=H, $NO_2$, CN, $CO_2H$, $NH_2$, halogens, alkyl, aryl, or heteroaryl;
- R2=H, $NO_2$, CN, $CO_2H$, $NH_2$, halogens, alkyl, aryl, heteroaryl, alcohols, or esters;
- R3=H, $NO_2$, CN, $CO_2H$, $NH_2$, halogens, alkyl, aryl, heteroaryl, amino alcohols, amino alkyls, alcohols, or esters;

and, wherein for the formula II:
- R1=H and R2=—$CH_2NHCH_2CH_2OH$ are used when preparing a pharmaceutical composition that acts by inhibiting the human phosphorylase uridine enzyme.

Use of the formulas I or II compounds as phosphorylase uridine enzyme inhibitors combined with at least one antineoplastic.

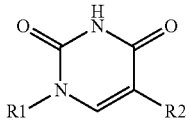

Formula I

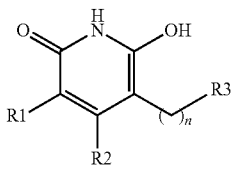

Formula II

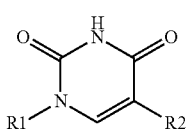

or its pharmaceutically acceptable salts
wherein, for the formula I, R1, R2, and R3 are independently chosen among:
- R1=H, $NO_2$, CN, $CO_2H$, $NH_2$, halogens, alkyl, aryl, or heteroaryl;
- R2=H, $NO_2$, CN, $CO_2H$, $NH_2$, halogens, alkyl, aryl, heteroaryl, alcohols, or esters;
- R3=H, $NO_2$, CN, $CO_2H$, $NH_2$, halogens, alkyl, aryl, heteroaryl, amino alcohols, amino alkyls, alcohols, or esters;

and, wherein for the formula II:
- R1=H and R2=—$CH_2NHCH_2CH_2OH$ combined with at least one antineoplastic.

In a preferred embodiment, the compounds used as phosphorylase uridine enzyme inhibitors are the Formula I compounds:

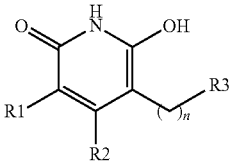

Formula I a) when R1=CN, R2=$CH_3$ and n=1, $R_3$=—$N(CH_3)_2$, —$NHCH_2CH_2OH$, H, (1,2-dihydroxypropan-3-yl)amino, piperidin-1-yl, (1,3-dihydroxypropan-2-yl)amino, —$N(CH_2CH_3)_2$, —$N(CH_2CH_2CH_3)_2$, or phenyl;
b) R1=CN, R2=phenyl, R3=H, and n=0;
c) R1=CN, R2=$CH_2CH_3$, R3=H, and n=0;
d) R1=CN, R2=H, R3=H, and n=0;
e) R1=CN, R2=$CH_3$, n=0, and the counter-ion of formula I is $K^+$;

In a most preferred embodiment, the compounds of formulas X, Y, or Z are used when preparing a pharmaceutical composition that acts by inhibiting the human phosphorylase uridine enzyme, combined or not with one antineoplastic.

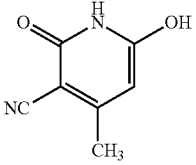

Formula X

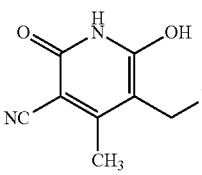

Formula Y

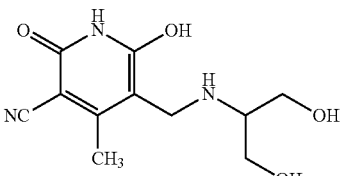

Formula Z

The compound of formula X is in a concentration from 300 nM to 600 nM, the compound of formula Y is in a concentration ranging from 58 nM to 78 nM, and the compound of formula Z is in a concentration range from 83 nM to 105 nM regarding the inhibition of the human phosphorylase uridine enzyme catalytic activity.

The formulas I or II compounds or, further, of the specific compounds with formulas X, Y, or Z, are used as phosphorylase uridine enzyme inhibitors, which inhibition acts in the antineoplastic effectivity increase and in the side effects reduction caused by the antineoplastic administration.

Preferentially, the antineoplastic used in the present invention is one pyrimidine analogue. Most preferentially, the antineoplastic is one fluoropyrimidine, as, for example, the 5-fluorouracil and the 5-fluoro-2'-deoxyuridine. In a preferred embodiment, the antineoplastic is the 5-fluorouracil, which is present in a concentration ranging from 100 mg/m$^2$ of the body surface to 600 mg/m$^2$ of the body surface. Most preferentially, the 5-fluorouracil is present in a range from 400 mg/m$^2$ to 600 mg/m$^2$ of the body surface.

The formulas I or II compounds or, further, of the specific compounds as formulas X or Y, are used as phosphorylase uridine enzyme inhibitors, which inhibition acts in several physiological disorders, these disorders indicated in the group consisting of: epilepsy, convulsions, Parkinson disease, Alzheimer disease, anxiety, sleeping disorders, infertility, ischemia, hypoxia, respiratory dysfunction, cardiovascular diseases, and hand-foot syndrome (palmar-plantar erythrodysesthesia) induced by chemotherapy.

In the present patent application, the compounds indicated by the formulas I and II increase the endogenous uridine levels that may lead to: the increase of the seizure activity for epilepsy cases; the potentiation of the dopaminergic neurotransmission of the central nervous system for Parkinson disease cases; interfere in the modulation of the GABAA-benzodiazepinic receptor for anxiety cases, increase of activation of the GABAA-benzodiazepinic receptors and barbiturates for sleeping disorders cases, increase of the sperm motility for infertility cases, increase of lipidic and glicidic metabolism preventing cellular necrosis for ischemia and hypoxia cases, and increasing the mucociliary epithelium activity and hydrating again the airways for respiratory dysfunction cases; and increase of endogenous uridine reducing the toxic effects of the chemotherapy that culminates in the hand-foot syndrome.

The examples here shown have the intent only of illustration of the numerous manners of performing the invention, however without limiting the scope thereof.

EXAMPLE 1

Preferred Embodiment

Selection In Vitro of the Human Phosphorylase Uridine 1 (hUP1) Inhibitors:

The enzymatic activity of the hUP1 is performed through the enzymatic essay using one spectrophotometer UV/visible where the absorbance reduction of uridine in 280 nm, for 1 min and at 37° C. was monitored.

For determining which inhibitors would be selected for determining the inhibition constant ($K_i$), one cut point of 1 µM was stipulated, where only those compounds that would inhibit more than 60% of the initial activity of the enzyme would be selected for this type of analysis (Table 1). From all compounds tested, 7 molecules had its inhibition above 60% with the concentration of 1 µM (Compounds c1, c2, c3, c4, c6, c12, and c13). All essays described on this patent application were performed for these compounds and for benzil acyclo uridine (BAU), in order to perform a direct comparison of the results achieved with the better in vitro inhibitor of the hUP1 described (standard).

Determining the $K_i$ for Leader Compounds:

Initially, it was performed the dependent-time essay in order to evaluate if the compound inhibition over the enzyme is affected over the time. It was verified that none of the compounds tested until the present moment presents dependent-time inhibition.

For determining $K_i$ for the selected inhibitors, we performed saturation curves where the concentration of one of the substrates is fixed next to the $K_m$ and the concentration of another, varied until the saturation in fixed-varying concentrations of each one of the inhibitors.

Through the double-reciprocal graphics generated by the analysis, we achieved straight standards allowing us to suggest the inhibition type (competitive, Not competitive, or uncompetitive) that the compound has over the enzyme, regarding each one of the substrates and the determination of its $K_i$ value (Table 1) using the equations I to III, indicated below:

$$v=VA/[K_a(1+I/K_{ii})+A] \quad (I)$$

$$v=VA/[K_a(1+I/K_{ii})+A(1+K_{is})] \quad (II)$$

$$v=VA/[A(1+I/K_{is})+K_a] \quad (III)$$

From the 7 compounds tested, the two best compounds were compounds c2 and c6, with $K_i$ values for uridine of 68 nM and 94 nM, respectively.

Regarding the inhibition profile, both showed having a competitive inhibition for uridine substrate and uncompetitive for substrate $P_i$, supporting the enzyme kinetic mechanism data, where $P_i$ is bonded first to the free enzyme for later binding of the uridine at the active site for forming the ternary complex (Renck et al., 2010). The compound c6 further had a characteristic different from further binders, providing the constant reduction of Michaelis-Menten ($K_m$) of the $P_i$ on half, this means that the binder increases twice the substrate affinity by active site of the enzyme. This event favors the inhibitor binding once its inhibition type is uncompetitive, it needs the $P_i$ is bonded previously to the enzyme active site for later binding. Regarding BAU, its constant inhibition for uridine described on the literature is 100 nM and this data was confirmed through experiments performed, allowing the direct comparison of our compounds efficiency.

In this way, through an overview of $K_i$ values and inhibition profiles, compounds with proximal values and even values smaller than the most potent inhibitor described in the literature up to now were achieved, reinforcing the importance thereof.

TABLE 1

Inhibitors of the enzyme hUP1 in vitro, commercial and synthetized.

| Compound | Inhibition with 1 μM (%) | $K_i$ for uridine (nM) | Inhibition type for uridine | $K_i$ for phosphate (nM) | Inhibiting type for phosphate |
|---|---|---|---|---|---|
| 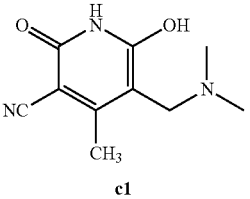 c1 | 81 | 99 ± 13 | Competitive | 107 ± 7 | Uncompetitive |
| 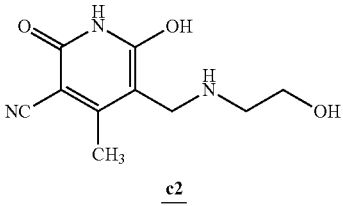 [SMILES: Cc1c(CNCCO)c(O)[nH]c(=O)c1C#N] c2 | 80 | 68 ± 10 | Competitive | 127 ± 8 | Uncompetitive |
| 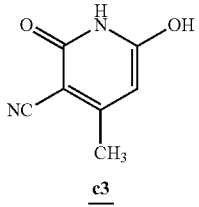 c3 | 70 | 375 ± 145/635 ± 91 | Not competitive | 332 ± 32 | Uncompetitive |
| 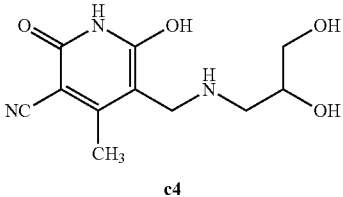 [SMILES: Cc1c(CNCC(O)CO)c(O)[nH]c(=O)c1C#N] c4 | 78 | 109 ± 10 | Competitive | 182 ± 7 | Uncompetitive |
| 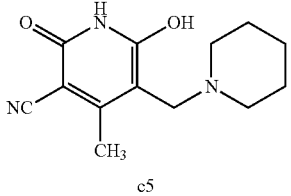 [SMILES: Cc1c(CN2CCCCC2)c(O)[nH]c(=O)c1C#N] c5 | 49 | — | — | — | — |
| 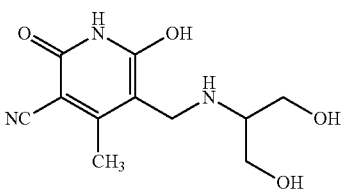 c6 | 82 | 94 ± 11 | Competitive | 98 ± 6 | Uncompetitive |

TABLE 1-continued
Inhibitors of the enzyme hUP1 in vitro, commercial and synthetized.
| Compound | Inhibition with 1 μM (%) | $K_i$ for uridine (nM) | Inhibition type for uridine | $K_i$ for phosphate (nM) | Inhibiting type for phosphate |
|---|---|---|---|---|---|
| 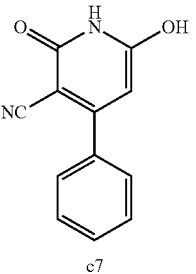 [SMILES: N#Cc1c(-c2ccccc2)cc(O)[nH]c1=O]<br>c7 | 42 | — | — | — | — |
| 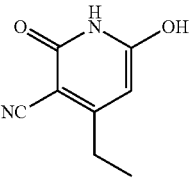<br>c8 | 25 | — | — | — | — |
| 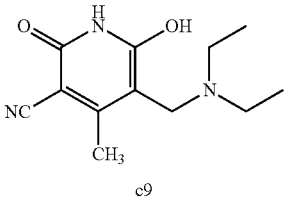 [SMILES: CCN(CC)Cc1c(O)[nH]c(=O)c(C#N)c1C]<br>c9 | 25 | — | — | — | — |
| 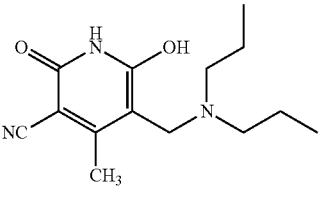<br>c10 | 20 | — | — | — | — |
| 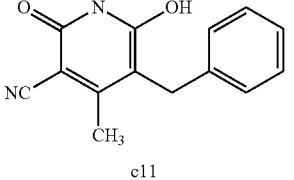<br>c11 | 43 | — | — | — | — |
| 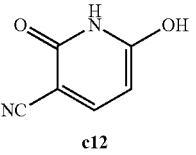<br>c12 | 67 | 2610 ± 339/2546 ± 330 | Not competitive | 565 ± 113/666 ± 59 | Not Competitive |

TABLE 1-continued

Inhibitors of the enzyme hUP1 in vitro, commercial and synthetized.

| Compound | Inhibition with 1 μM (%) | $K_i$ for uridine (nM) | Inhibition type for uridine | $K_i$ for phosphate (nM) | Inhibiting type for phosphate |
|---|---|---|---|---|---|
| 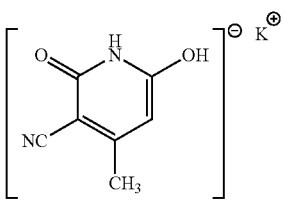 c13 | 62 | 885 ± 183/897 ± 65 | Not competitive | 908 ± 262/974 ± 75 | Not competitive |
| 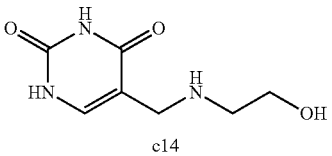 [SMILES: O=c1[nH]cc(CNCCO)c(=O)[nH]1] c14 | 2 | — | — | — | — |
| 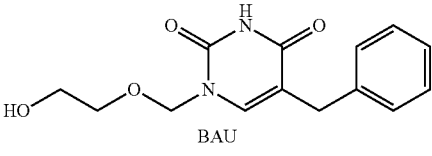 BAU c15 | — | 130 ± 21 | Competitive | 547 ± 44/317 ± 61 | Not competitive |

In bold are the compounds presenting inhibition above 60% with 1 μM and were selected for determining the thermodynamic parameters. In bold and underlined the compounds are in vivo tests.

Determining the Thermodynamic Parameters:

For determining the thermodynamic parameters (enthalpy variation—ΔH, entropy variation—ΔS, and free energy variation of Gibbs—ΔG) were performed compounds binding essays to the enzyme in different conditions: free enzyme, complexed enzyme with the substrate $P_i$, and the complexed enzyme with the product ribose-1-phosphate (R1P). For such analyses, it was used isothermal titration microcalorimetry (ITC) where the equipment monitors the difference of transferred heat, between the reference cell and the sample cell, when bindings are formed or broken during the binding process. The data analysis achieved was performed through the model One Set of Sites and the determination of ΔG and the dissociation constant ($K_D$) were through the equations (IV) and (V) below, respectively:

$$\Delta G = \Delta H - T\Delta S \quad (IV)$$

$$K_D = 1/K_a \quad (V)$$

Through the negative values of ΔG it may suggest that the binding of these compounds to the enzyme is spontaneous, as well through the negative values of ΔH, it may suggest that there is a strong iteration through polar bindings. The compounds analyzed show one of the greatest biological problems in the new molecules drawing, which is the compensatory system ΔH–ΔS, generating compounds with the same free energy values of Gibbs and, consequently, with the same affinity. In comparison with BAU, the analyzed compounds present better enthalpy values, indicating a greater complex stability through hydrogen bindings and van der Waals bindings. However, regarding the entropy values, the present compounds may also improve regarding the BAU, and may suggest that is also possible to perform modifications adding hydrophobic branches to the molecule, mainly by the presence of one hydrophobic pocket comprising the uracil active site. $K_D$ values found through ITC support $K_i$ values found, as well the better binding condition of the compounds to the enzyme (binding the free shape of complexed of the enzyme) support the inhibition profile achieved. All thermodynamic parameters are found on Table 2 below.

TABLE 2

Thermodynamic parameters of the selected compounds.
Highlighted items are the best binding conditions for each one of the compounds to the enzyme.

| Compound | hUP1 or complex | ΔH° (kcal/mol) | −TΔS (kcal/mol/deg) | ΔG° (kcal/mol) | $K_D$ (nM) |
|---|---|---|---|---|---|
| c1 | hUP1 | −6.7 ± 0.2 | 0.8 ± 0.1 | −7.6 ± 1.1 | 4200 ± 602 |
|  | hUP1-$P_i^a$ | −12 ± 0.2 | 2.6 ± 0.6 | −9.1 ± 2.1 | 312 ± 73 |
|  | hUP1-R1P 50 μM | −22 ± 0.4 | 14 ± 0.7 | −7.2 ± 0.4 | 7400 ± 381 |
|  | hUP1-R1P 150 μM | −23 ± 0.1 | 16 ± 2.1 | −7.0 ± 0.9 | 10000 ± 1325 |

TABLE 2-continued

Thermodynamic parameters of the selected compounds.
Highlighted items are the best binding conditions for each one of the compounds to the enzyme.

| Compound | hUP1 or complex | $\Delta H°$ (kcal/mol) | $-T\Delta S$ (kcal/mol/deg) | $\Delta G°$ (kcal/mol) | $K_D$ (nM) |
|---|---|---|---|---|---|
| c2 | hUP1 | −23 ± 0.5 | 14 ± 1.5 | −8.0 ± 0.9 | 2000 ± 221 |
|  | hUP1-$P_i^a$ | −16 ± 0.2 | 6.4 ± 1.4 | −9.5 ± 2.1 | 151 ± 34 |
|  | hUP1-R1P 50 µM | −17 ± 0.6 | 9.5 ± 1.7 | −8.0 ± 1.5 | 2300 ± 423 |
|  | hUP1-R1P 150 µM | −30 ± 1.5 | 23 ± 3.3 | −7.6 ± 1.1 | 3800 ± 553 |
| c3 | hUP1 | — | — | — | — |
|  | hUP1-$P_i$ | −19 ± 1.3 | 12 ± 1.4 | −6.9 ± 0.8 | 12000 ± 1395 |
|  | hUP1-R1P 50 µM | −31 ± 1.2 | 22 ± 5.4 | −8.3 ± 2.0 | 1400 ± 341 |
|  | hUP1-R1P 150 µM | −21 ± 0.1 | 11 ± 1.5 | −9.8 ± 1.4 | 40 ± 5.0 |
|  | hUP1-R1P 200 µM$^a$ | −22 ± 0.1 | 11 ± 1.3 | −11 ± 1.3 | 20 ± 2.0 |
| c4 | hUP1 | −22 ± 2.2 | 15 ± 2.0 | −6.7 ± 0.9 | 20000 ± 2633 |
|  | hUP1-$Pi^a$ | −19 ± 0.1 | 10 ± 1.0 | −9.3 ± 0.9 | 263 ± 26 |
|  | hUP1-R1P 50 µM | −22 ± 0.5 | 14 ± 1.0 | −7.5 ± 0.5 | 4600 ± 344 |
|  | hUP1-R1P 150 µM | −18 ± 0.8 | 11 ± 1.2 | −7.1 ± 0.8 | 9400 ± 1037 |
| c6 | hUP1 | −24 ± 0.6 | 16 ± 2.0 | −7.4 ± 1.0 | 5300 ± 674 |
|  | hUP1-$P_i^a$ | −14 ± 0.2 | 5.0 ± 0.8 | −9.0 ± 1.5 | 502 ± 83 |
|  | hUP1-R1P 50 µM | −18 ± 0.4 | 10 ± 1.0 | −7.3 ± 0.7 | 7000 ± 661 |
|  | hUP1-R1P 150 µM | −10 ± 1.0 | 3.3 ± 1.0 | −7.3 ± 2.2 | 7000 ± 2115 |
| c12 | hUP1 | −9.6 ± 0.3 | 1.7 ± 0.3 | −7.8 ± 1.5 | 2900 ± 554 |
|  | hUP1-$P_i$ | — | — | — | — |
|  | hUP1-R1P 50 µM$^a$ | −15 ± 0.1 | 5.7 ± 0.9 | −9.8 ± 1.6 | 108 ± 18 |
|  | hUP1-R1P 150 µM | −18 ± 0.5 | 8.5 ± 3.2 | −9.7 ± 3.7 | 127 ± 48 |
| c13 | hUP1 | −8.7 ± 0.7 | 1.7 ± 0.2 | −6.9 ± 1.0 | 12000 ± 1822 |
|  | hUP1-$P_i$ | — | — | — | — |
|  | hUP1-R1P 50 µM | −27 ± 0.7 | 19 ± 2.9 | −8.1 ± 1.2 | 1300 ± 197 |
|  | hUP1-R1P 150 µM | −35 ± 2.1 | 27 ± 9.1 | −8.0 ± 2.7 | 1297 ± 435 |
| BAU | hUP1 | −10 ± 0.1 | 1.5 ± 0.2 | −8.4 ± 1.0 | 1200 ± 150 |
|  | hUP1-$P_i$ | −13 ± 0.3 | 4.6 ± 0.8 | −8.2 ± 1.4 | 1400 ± 239 |
|  | hUP1-R1P 50 µM | −12 ± 0.3 | 4.3 ± 0.9 | −8.2 ± 1.7 | 1200 ± 244 |
|  | hUP1-R1P 150 µM | −20 ± 0.7 | 12 ± 1.6 | −7.3 ± 1.0 | 6600 ± 898 |

$^a$better binding conditions.

Test in Cell Culture with Compounds c2 and c3

For cell culture tests, two tumor lines of colon (HT-29 and SW-620) and one normal line of keratinocytes (HaCat) were selected. HaCat cells were cultivated in Eagle medium modified by Dulbecco (DMEM) while the HT-29 and SW-620 cells were cultivated in RPMI 1640 medium, both with 2 mM of L-glutamine, supplemented with 10% of fetal bovine serum, 150 U/ml of penicillin, 150 µg/ml of streptomycin and kept in wet incubator at 37° C. and 5% of $CO_2$.

In the FIG. 1, the results of the normal cells HaCat (in A and D), in the tumor cells HT-29 (in B and E) and in tumor cells SW-620 (C and F) are presented. The statistic analysis was performed through one-way ANOVA followed by the Bonferroni test. The lines represent the standard error while each of column represents the mean of the three independent experiments performed in quadruplicate.

For the cytotoxicity analysis of the compounds in the lines mentioned above, the compounds were added to the cells, bonded to 96-well plates ($7\times10^3$ cells/well), in the concentrations of 1-3-10-30-100 µM, for 72 h of incubation. The results were achieved through the colorimetric method with bromide 3-(4,5-dimethyl-2-thiazolyl)-2,5-dimethyl tetrazolium (MTT), where the MTT oxidation in its MTT-formazan product is proportional to the mitochondrial activity and, then, to the cell viability. With the desired, the compounds were not cytotoxic against the tumor lines HT-29 and SW-620 neither against the normal line HaCat (FIG. 1).

Evaluation of the Compounds Effect Over the 5-FU Cytotoxicity

The analysis of the possible effects of the compounds over the dependent-dose curve of the 5-FU was performed with the same cell lines described above, in order to make a comparison between normal lines and tumor lines.

Firstly, it was determined the concentration value of 5-FU inhibiting 50% of the cell growth ($IC_{50}$) without the presence of compounds. For that, different concentrations of 5-FU were added to the cells ($7\times10^3$ cells/well) in 96-well plates: HaCat (0.25-20 µM), HT-29 (0.25-50 µM) and SW-620 (0.5-150 µM). The cells were exposed to the chemotherapeutic for the period of 72 h. The same dose-answer curve was made in the presence of 30 µM of the compounds c2 and c3, then used the inhibitor BAU as positive control for inhibiting the phosphorylase uridine.

Figure 2A:
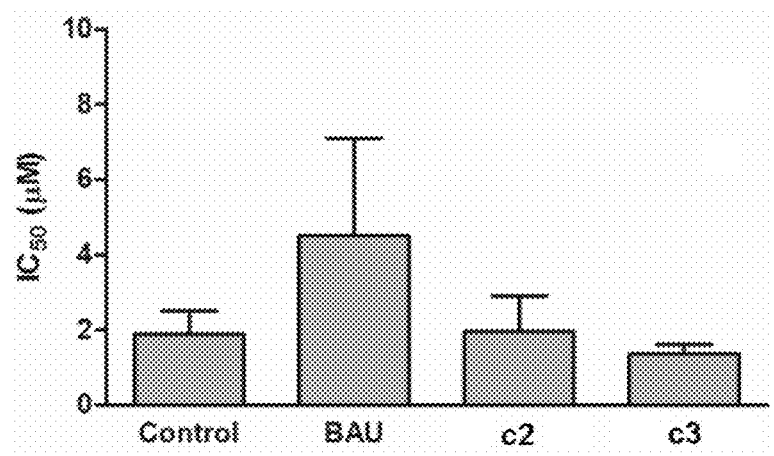
FIG. 2A shows the analysis of the effect of compounds on cell sensitivity to the 5-FU, particularly over the normal cell line HaCat.

For the analysis of cell sensibility to the 5-FU, it was used the MTT method (described above) and expressed in the forma $IC_{50}$ form which was calculated from the semi logarithmic curve. From the graphs, we verified that $IC_{50}$ values for normal line HaCat was kept similar, with no significant difference between the control curve and the curves with the compounds (FIG. 2A). The statistical analysis was performed through one-way ANOVA followed by the Bonferroni test. The lines represent the standard error while each column represents the mean of the three independent experiments performed in quadruplicate. *Significant difference regarding the control (*$p<0.05$) and (**$p<0.01$), as indicated in the FIG. 2A.

Figure 2B:
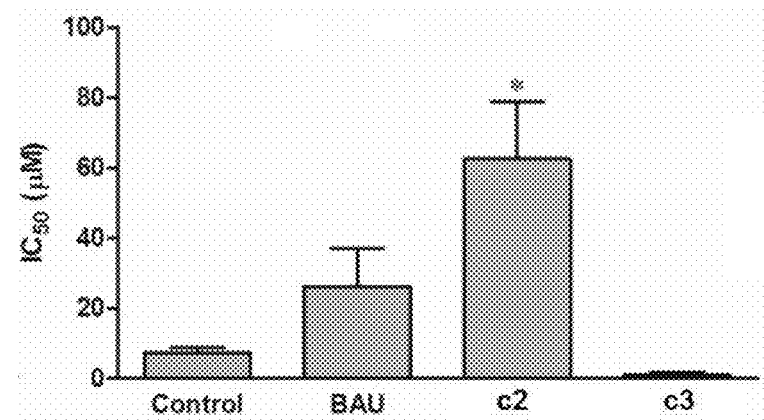
FIG. 2B shows the analysis of the effect of compounds on cell sensitivity to the 5-FU, particularly over the tumor cell line HT-29.

In the less aggressive tumor line HT-29, we verified that the compound c2 developed one protection effect to cell sensibility against 5-FUra, increasing $IC_{50}$ value for this cell type (FIG. 2B). The statistical analysis was performed through one-way ANOVA followed by Bonferroni test. The lines represent the standard error while each column represents the mean of the three independent experiments performed in quadruplicate. *Significant difference regarding the control (*$p<0.05$) and (**$p<0.01$), as indicated in the FIG. 2B.

Figure 2C:
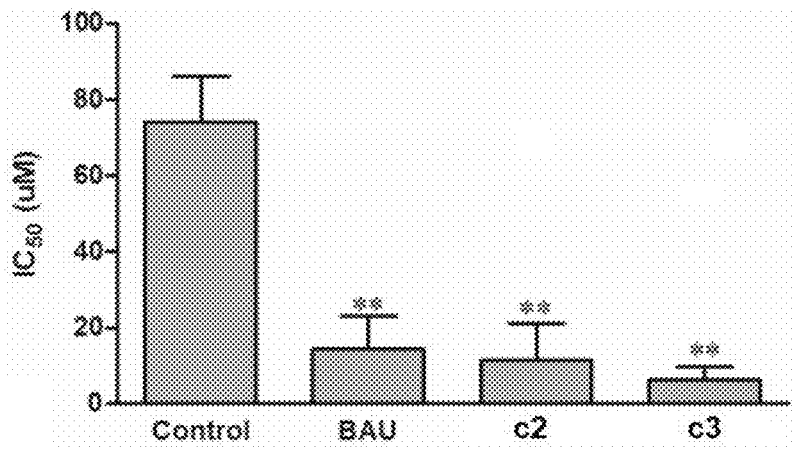
FIG. 2C shows the analysis of the effect of compounds on cell sensitivity to the 5-FU, particularly over the tumor cell line SW-620.

In an interesting way, in the most aggressive tumor cells (SW-620), the compounds reduced significantly the $IC_{50}$ value of 5-FU (FIG. 2C) showing that the presence of these compounds make the cells more sensible to the chemotherapeutic; suggesting, in this way, that the conversion blockage of the 5-FU in 5-FUrd performed by the hUP, allows more than 5-FU remain available to be converted into FdUMP and inhibit the enzyme TS, causing its damage therapeutic effect to the DNA. In this way, the compounds of the present invention act additionally in the antineoplastic effectivity increase. The statistical analysis was performed through one-way ANOVA followed by Bonferroni test. The lines represent the standard error while each column represents the mean of the three independent experiments performed in quadruplicate. *Significant difference regarding the control (*$p<0.05$) and (**$p<0.01$), as indicated in the FIG. 2C.

Compound c3 Test in Rodents:

The compound c3 was tested in in vivo for evaluating its protection regarding intestinal mucositis caused by 5-FU.

The mucositis model was developed in female Wistar mouse (180-200 g) and the animals were divided into 5 groups with 4 animals in each group:

Group 1: Saline+Saline
Group 2: Compound c3 (150 mg/kg)+saline
Group 3: Saline+5-FU (50 mg/kg)
Group 4: Compound c3 (50 mg/kg)+5-FU (50 mg/kg)
Group 5: Compound c3 (150 mg/kg)+5-FU (50 mg/kg)

The test compound was administrated via oral, 30 minutes before administrating the chemotherapeutic 5-FU that was administrated via intraperitoneal. This treatment was followed for 5 days with once a day administrations. In the $5^{th}$ treatment day, the animals were euthanized using one inhalational anesthetic (isoflurane) and the initial portion of the intestine (corresponding to jejunum and ileus) was collected for myeloperoxidase analysis (MPO) and histological analysis of the tissue, as well blood collect for quantification analysis of the uridine in the plasma. The animals were also followed-up regarding weight loss and diarrhea.

Figure 3:
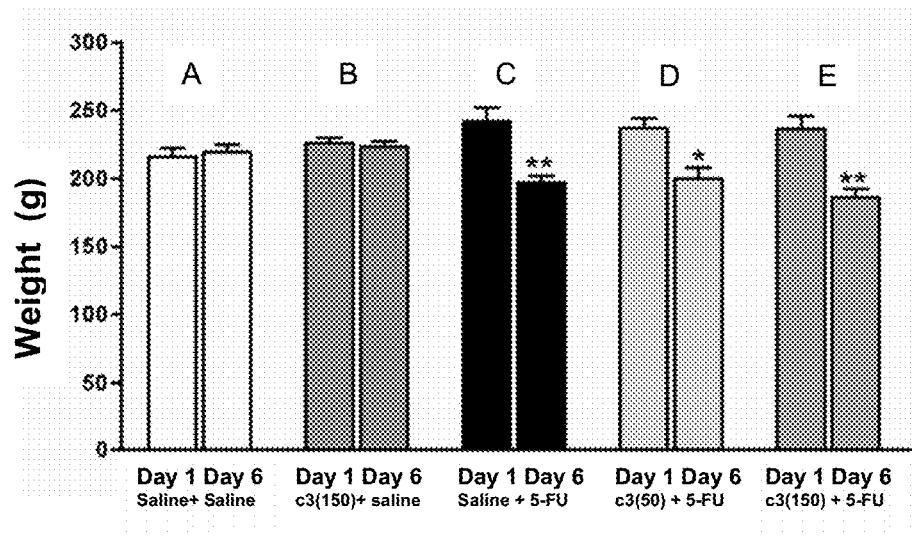
FIG. 3 shows the analysis of the weight between day 1 and day 6. A—corresponds to the group 1, B—corresponds to the group 2, C—corresponds to the group 3, D—corresponds to the group 4, and E—corresponds to the group 5.

Regarding weight loss, all animals that received 5-FU, either with or without the compound, had a weight loss and this was significant (FIG. 3). In the same manner, all groups that received the chemotherapeutic developed severe diarrhea. In these parameters, the compound was not able to avoid these side effects. The statistical analysis was performed though one-way ANOVA followed by Bonferroni test. The lines represent the standard error while each column represents the weights mean of the 4 animals in each group. *Significant difference regarding the first day (*$p<0.05$) and (**$p<0.01$), as indicated in the FIG. 3.

Figure 4:
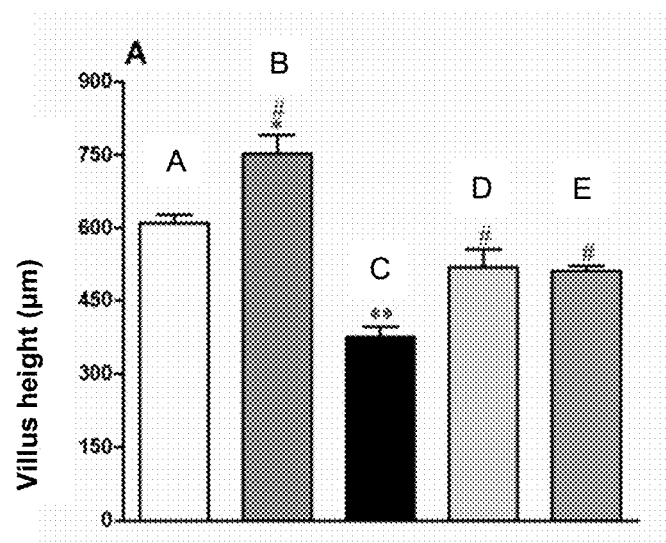
FIG. 4 shows the analysis of the histological intestinal villus. In A—group 1, in B—group 2, in C—group 3, in D—group 4, and in and—group 5.

However, when performing the histological analysis, it was verified that the groups that received the compound, in both tested doses, had the intestinal villus size statistically equal to the group Saline and different from the group 5-FU, while the group that received only 5-FU had its villus totally damaged (FIG. 4). In the FIG. 4, the statistical analysis was performed though one-way ANOVA followed by Bonferroni test. The lines represent the standard error while each column represents the mean of three different fields of each one of the 4 animals of the group. #Significant difference regarding group 3, *Significant difference regarding group 1 (#$p<0.001$) and (**$p<0.0001$).

The data achieved and indicated in the FIG. 4 are extremely important since the intestinal villus are responsible for absorbing water and nutrients of the organism also causing the intestinal epithelium is more integrate and then reducing the mucositis degree.

Figure 5A:
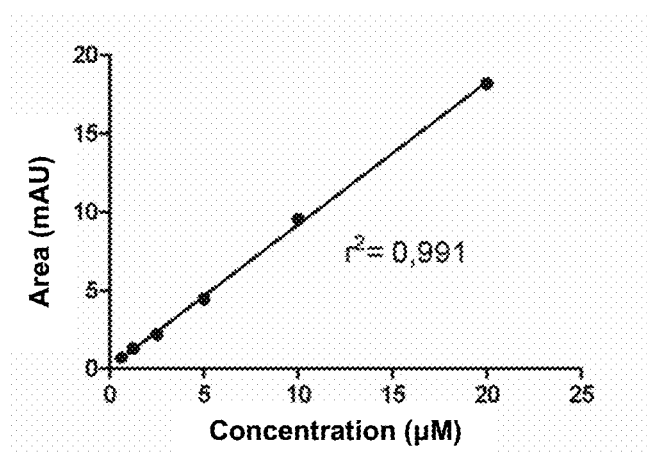
FIG. 5A shows the uridine standard curve.
Figure 5B:
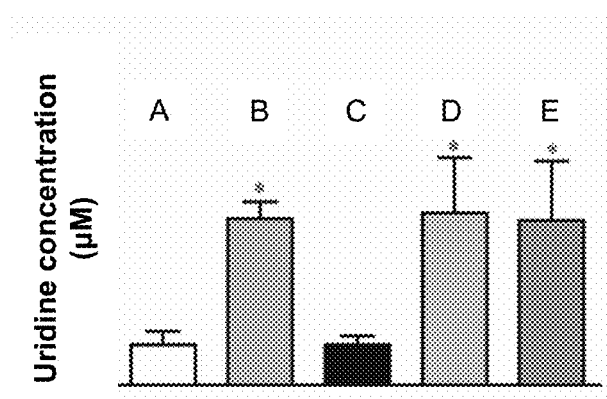
FIG. 5B shows the analysis of the plasma uridine concentration. In A—group 1, in B—group 2, in C—group 3, in D—group 4, and in and—group 5.

The determination of the uridine concentration in the animals' plasma as performed by HPLC, using as mobile phase acetic acid 0.1%. First, it was made a calibration curve using commercial uridine as standard (Sigma) in the concentrations of 0.625-1.25-2.5-5.0-10.0-20.0 µM in mice plasma to keep the same matrix where the samples ones are. After the calibration curve, the plasma samples were analyzed of each group and was one positive result was achieved. As was expected, there was an increase of 4.4 times in the uridine concentration in the animals' plasma that received the compound orally, either in the dose of 50 mg/kg or in the dose of 150 mg/kg (FIGS. 5A and 5B). From this data, it is possible to suggest that the protection effect seen in the intestinal epithelium of the animals regarding the chemotherapeutic aggression was due to the protection effect generated by the uridine. In the FIG. 5B, the statistical analysis was performed though one-way ANOVA followed by Bonferroni test. The lines represent the standard error, while each column represents the mean of the concentration in each one of the 4 animals of each group. *Significant difference regarding group 1 (*$p<0.05$) and (**$p<0.01$).

Figure 6:
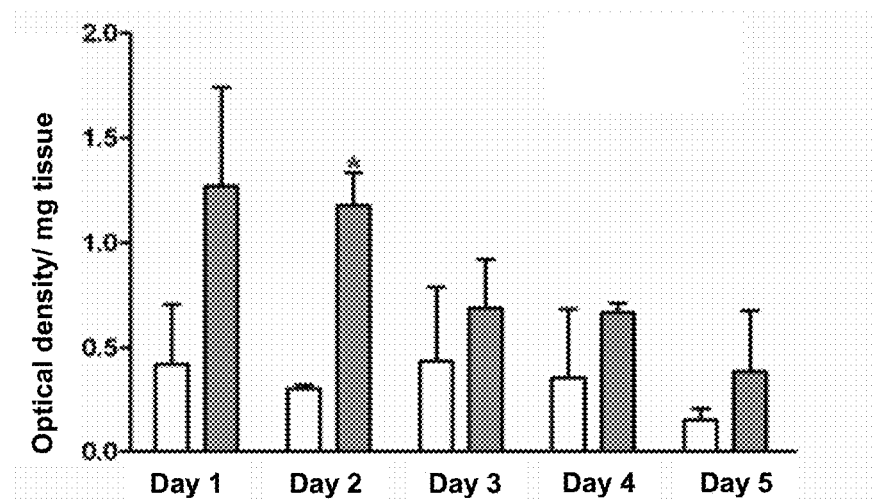
FIG. 6 shows the MPO analysis in different days of euthanasia. In white saline group and in gray group treated with 5-FUra (50 mg/kg).

The last in vivo analysis was regarding the MPO. The MPO is a primary answer of inflammation, present in neutrophils, and for that it was analyzed which is the best day of euthanasia to check this primary answer. The treatment schema lasted 5 days, where the animals were divided into 2 groups with 10 animals in each (Group Saline and Group 5-FU). The 5-FU (50 mg/kg) was administrated using the intraperitoneal via, as well the Saline. The animals were put into euthanasia in 24 h, 48 h, 72 h, 96 h and 120 h after the administration (days 1-5) and the initial portion of the intestine was collected. It was verified that the best day for MPO quantification would be day 2 (48 h after 5-FU administration), such as represented in the FIG. 6, in which the statistical analysis was performed though one-way ANOVA followed by Bonferroni test. The lines represent the standard error while each column represents the mean of two animals of each group. *Significant difference regarding group Saline (*$p<0.05$).

Figure 7:
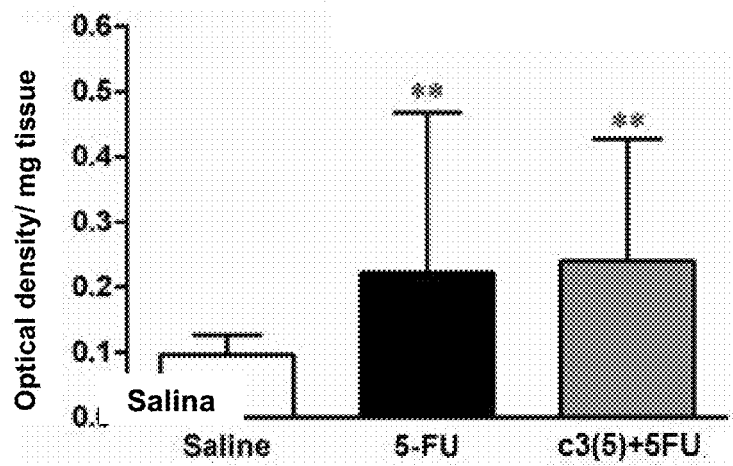
FIG. 7 shows the MPO analysis in mucositis model.

The first experiment of mucositis was repeated, with 3 groups having 5 animals in each (Group Saline+Saline, Group Saline+5-FU and Group Compound c3+5-FU). The compound had its administration beginning 2 days before the 5-FU, of 8-8 h, orally, in the dose of 50 mg/kg; and followed in the other 2 days with the chemotherapeutic. The animals were euthanized with isoflurane and the initial portion of the intestine was analyzed. It was verified that the compound was not able to revert the primary inflammation process (FIG. 7), which supports the weight loss the animals had even with the villus conservation. In the FIG. 7, the statistical analysis was performed though one-way ANOVA followed by Bonferroni test. The lines represent the standard error while each column represents the mean of five animals for each group. *Significant difference regarding group Saline (**$p<0.01$).

Those skilled in the art will appreciate the knowledge here presented and may reproduce the invention in the embodiments presented and in other variants, covered in the attached claims scope.

What is claimed is:

1. A process for inhibiting the human phosphorylase uridine enzyme comprising administering to a subject a compound of formula I

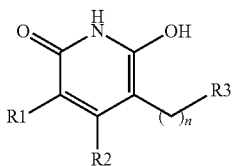

Formula I or its pharmaceutically acceptable salts;
wherein n=0 or 1;
wherein, for the formula I, R1, R2, and R3 are independently chosen between:
a) when R1=CN, R2=CH₃ and n=1, R3=—N(CH₃)₂, —NHCH₂CH₂OH, H, (1,2-dihydroxypropan-3-yl) amino, piperidin-1-yl, (1,3-dihydroxypropan-2-yl) amino, —N(CH₂CH₃)₂, —N(CH₂CH₂CH₃)₂, or phenyl;
b) R1=CN, R2=phenyl, R3=H, and n=0;
c) R1=CN, R2=CH₂CH₃, R3=H, and n=0;
d) R1=CN, R2=H, R3=H, and n=0; and
e) R1=CN, R2=CH₃, n=0, and the counter-ion of the formula I is K⁺.

2. The process according to claim 1, comprising administering the compound of formula I or its pharmaceutically acceptable salts combined with at least one antineoplastic.

3. The process according to claim 1, wherein the compound has the formula X, Y, or Z:

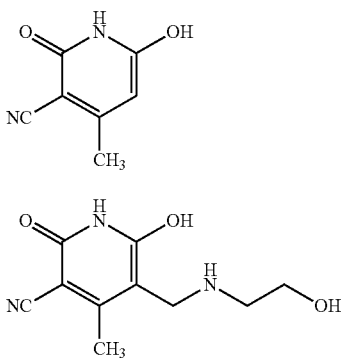

Formula X

Formula Y

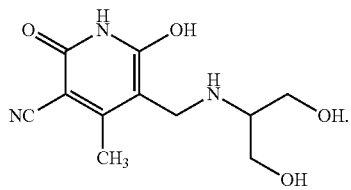

Formula Z

4. The process according to claim 3, wherein the compound of formula X is administered in a concentration range from 300 nM to 600 nM, the compound of formula Y is administered in a concentration range from 58 nM to 78 nM, and the compound of formula Z is administered in a concentration range from 83 nM to 105 nM, regarding the human phosphorylase uridine enzyme inhibition.

5. The process according to claim 1, wherein inhibiting the human phosphorylase uridine enzyme acts in the antineoplastic effectivity increase.

6. The process according to claim 1, wherein inhibiting the human phosphorylase uridine enzyme acts in the side effects reduction caused by antineoplastic administration.

7. The process according to claim 6, wherein the side effect is mucositis.

8. The process according to claim 2, wherein the antineoplastic is a fluoropyrimidine.

9. The process according to claim 2, wherein the antineoplastic is 5-fluorouracil or 5-fluoro-2'-deoxyuridine.

10. The process according to claim 9, wherein the 5-fluorouracil is in a concentration ranging from 100 mg/m² of body surface to 600 mg/m² of body surface.

11. The process according to claim 1, wherein inhibiting the human phosphorylase uridine enzyme acts in the treatment of the physiological disorders group consisting of: epilepsy, convulsions, Parkinson disease, Alzheimer disease, anxiety, sleeping disorders, infertility, ischemia, hypoxia, respiratory dysfunction, cardiovascular diseases, and hand-foot syndrome (palmar-plantar erythrodysesthesia) induced by chemotherapy.

* * * * *